United States Patent [19]

Wu et al.

[11] Patent Number: 5,062,995
[45] Date of Patent: Nov. 5, 1991

[54] POLYMERIC CARBAMATE DETERGENT BUILDERS

[75] Inventors: Shang-Ren Wu, Mahwah; Albert Garofalo, Whippany, both of N.J.

[73] Assignee: Lever Brothers Company, Division of Conopco, Inc., New York, N.Y.

[21] Appl. No.: 475,660

[22] Filed: Feb. 6, 1990

[51] Int. Cl.$^5$ ............ C02F 5/12; C11D 7/32; C11D 3/33
[52] U.S. Cl. ............ 252/546; 252/180; 252/181; 252/527; 252/DIG. 11; 526/301
[58] Field of Search ............ 252/DIG. 11, 180, 181, 252/546, 527; 526/301

[56] References Cited

U.S. PATENT DOCUMENTS

| | | | |
|---|---|---|---|
| 3,285,886 | 11/1966 | Gunderson | 252/180 |
| 3,308,067 | 3/1967 | Diehl | 252/558 |
| 3,331,773 | 7/1967 | Gunderson | 252/82 |
| 3,689,436 | 9/1972 | Stamm | 252/545 |
| 3,711,458 | 1/1973 | Olofson | 260/112.5 |
| 3,835,109 | 9/1974 | Olofson | 260/112.5 |
| 3,923,742 | 12/1974 | Haschke | 260/67 UA |
| 4,559,159 | 12/1985 | Denzinger | 252/174.24 |
| 4,740,314 | 4/1988 | Kneller | 252/180 |
| 4,797,223 | 1/1989 | Amick | 252/174.23 |

FOREIGN PATENT DOCUMENTS 2612521 9/1988 France .

Primary Examiner—Paul Lieberman
Assistant Examiner—Alexander G. Ghyka
Attorney, Agent, or Firm—James J. Farrell

[57] ABSTRACT

Novel vinyl carbamates, prepared from vinyl chloroformate and amino acids and polymers containing from 5–100% of these novel vinyl carbamates are disclosed. These polymers act as sequestering agents and are useful as detergency builders. Detergent compositions incorporating the polymers can be prepared without use of phosphorus-containing detergent builders.

Formulas for the novel carbamates and polymers are as follows:

Vinyl carbamate compounds of the Formula:

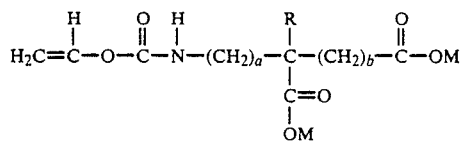

wherein a and b are independently 0, 1, or 2, or even greater; R is hydrogen methyl, ethyl or long chain alkyl, alkenyl or aryl and M is $C_{1-4}$ alkyl, hydrogen, or a cation which forms a substantially water soluble salt with said compound at ambient temperatures; and Polymeric compounds of the formula:

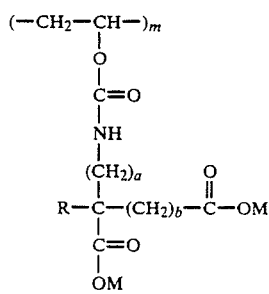

wherein a and b are independently 0, 1 or 2 or even greater; m is at least one; R is hydrogen, methyl, ethyl, or long chain alkyl, alkenyl or aryl and M is $C_{1-4}$ alkyl, hydrogen, or a cation which forms a substantially water soluble salt with said polymeric compound at Polymeric compounds with repeating units of the structure:

(Abstract continued on next page.)

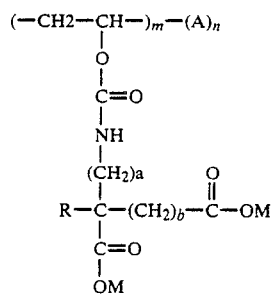

wherein a and b are independently 0, 1 or 2 or even greater; wherein m and n are at least one; R is hydrogen, methyl, ethyl, or long chain alkyl, alkenyl or aryl and M is hydrogen or a cation which forms a substantially water soluble salt with said polymeric compound at ambient temperatures or $C_{1-4}$ alkyl and wherein A is a repeating unit having at least one copolymerized comonomer, said comonomers being selected from the group consisting of unsaturated carboxylic acids and their salts, esters and derivatives, unsaturated dicarboxylic acids and their salts, esters, and derivatives, unsaturated alcohols, unsaturated amines, unsaturated pyrrols, vinyl ethers, alkyl acrylates, alkenyl carboxylalkyl ethers, vinyl esters of carboxylic acids, olefins and furans.

49 Claims, 1 Drawing Sheet

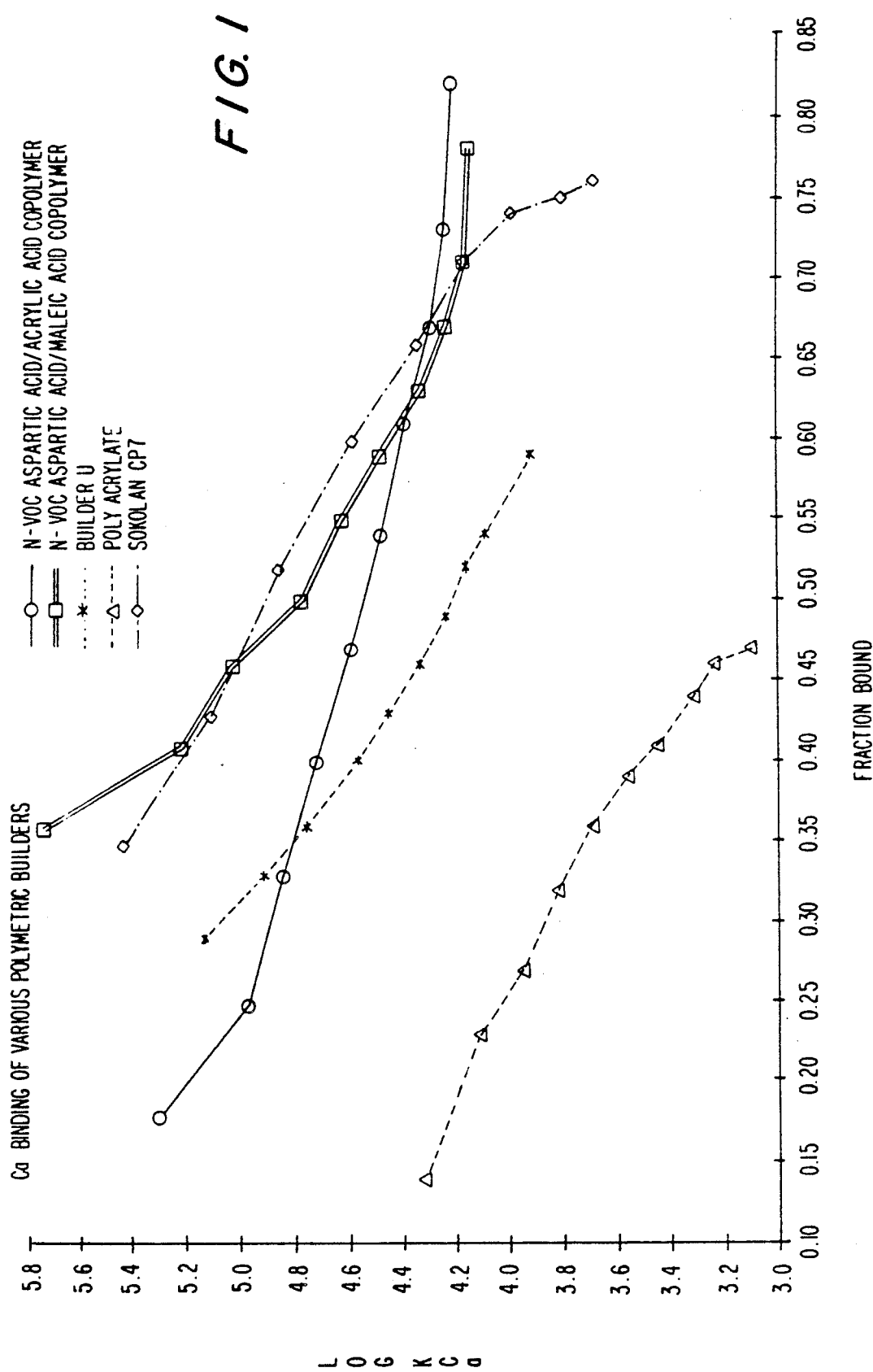

POLYMERIC CARBAMATE DETERGENT BUILDERS

FIELD OF THE INVENTION

The present invention relates to novel vinyl carbamates and polymers including these vinyl carbamates. These novel compounds are effective chelating agents and useful in detergent compositions. These polymers may also be used as anti-redeposition agents, dispersants, scale inhibitors, bleach stabilizing agents and in a variety of other applications which require hardness sequestration or crystal modification.

BACKGROUND OF THE INVENTION

Builders are desirable ingredients in powdered detergent formulations, which optimize the effectiveness of surfactants by sequestering calcium, magnesium and other 'hardness' ions present in the wash water that adversely affect detergency.

The manner in which detergent builders improve the cleaning powers of detergent compositions is related to a combination of factors such as emulsification of soil particles, solubilization of water insoluble materials, promotion of soil suspension in the wash water so as to retard soil redeposition, sequestration of metallic ions, and the like.

Phosphates, such as tripolyphosphates and pyrophosphates, are widely used as builders due to their excellent ability to sequester 'hardness' ions. However, the effect of phosphates upon the eutrophication of lakes and streams has been questioned and their use in detergent compositions has been subject to government scrutiny and regulation. Alternatives for phosphates are widely used by detergent formulators as builders in detergent formulations. Compositions and materials change frequently as formulators attempt to improve cleaning performance while offering greater convenience in handling at lower material cost. The industry has made substantial efforts to find suitable substitutes for phosphates, however, all have one or more drawbacks that offset their value in the formulations French Patent Specification 2,612,521 to Bernard Brosse discloses selected chelating polymers similar to those of the invention.

U.S. Pat. Nos. 3,711,458, and 3,835,109 to Olofson disclose processes for peptide synthesis employing a vinyloxy carbonyl group as a protecting group.

U.S. Pat. No. 3,923,742 to Haschke discloses a process for producing a polycarboxylate phosphate substitute said to be readily biodegradable.

U.S. Pat. No. 4,559,159 to Denzinger et al. discloses water soluble copolymers for use with detergents.

While polymeric carboxylates have been found to be suitable builders, few have been found to be biodegradable, indeed, few synthetic polymers have been found to be biodegradable. One method of improving the biodegradability of synthetic polymers has been to incorporate hydrolyzable linkages within the main polymer backbone. This approach, however, usually does not produce high molecular weight polymers. A second method of improving biodegradability is a method of this invention to couple relatively small biodegradable carboxylates to a polymer backbone which will, through hydrolyzable linkages, break down to form polyvinyl alcohol (PVA) or a PVA-like copolymer. Upon hydrolysis, the components are then expected to be biodegradable.

The polymeric builders herein described contain carbamate linkages with environmentally acceptable amino acids. While not wishing to be bound by theory, it is theorized that the carbamate linkages will break down in the environment to polyvinyl alcohol and the corresponding amino acid, both of which are reported be relatively environmentally acceptable. Further, the electrostatic and site specific charge interactions of the compounds of this invention contribute to the builder efficiency.

Accordingly, it is an object of the present invention to provide a novel class of effective 'hardness' ion sequestering agents which may be employed in detergent compositions as a replacement, in whole or in part, for phosphate builders.

A further object of the present invention is to provide detergent compositions employing these effective, non-phosphate builders.

Yet another object is to improve the biodegradability of selected polymers.

SUMMARY OF THE INVENTION

The invention broadly includes novel compounds, novel polymers, and methods of enhancing the biodegradability of selected polymers.

The novel compounds are vinyl carbamates of the general Formula:

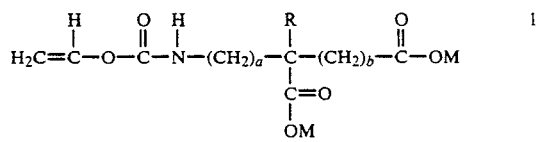

wherein a and b are independently 0, 1, or 2, or even greater; R is hydrogen, methyl, ethyl or long chain alkyl, alkenyl or aryl and M is $C_{1-4}$ alkyl, hydrogen or a cation such as ammonium, alkali metal; for example, sodium or potassium or indeed any cation which forms a substantially water soluble salt with the compound of Formula 1 as well as short chain alkyl groups of 1 to 4 carbon atoms.

Preferably, when a is 0, b is 0 or 2 and R is hydrogen; when a is 0, and b is 1, R is hydrogen or methyl and when a is 1, and b is 0, R is again hydrogen.

Another aspect of the invention are the homopolymers formed from the novel vinyl carbamates of Formula 1. Polymers of these novel vinyl carbamates are prepared via known methods. The homopolymers have the general Formula:

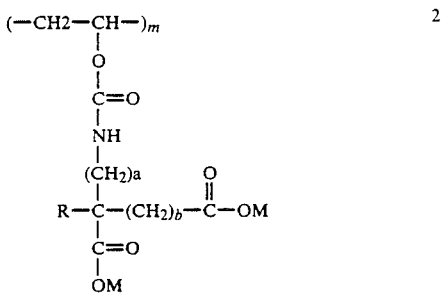

wherein a, b, R, and M are as defined above in Formula 1 and wherein m represents the number of repeating units in the polymer. As stated above, the polymers must be sufficiently water soluble to function as a builder to sequester hardness ions such as calcium, magnesium and the like.

Polymers may be prepared by free radical homopolymerization of these novel vinyl carbamates or by copolymerization with one or more other ethylenically unsaturated polymerizable comonomers. Thus, polymers containing two, three or even more comonomers, may be employed. Copolymers comprise repeating units of the Formula:

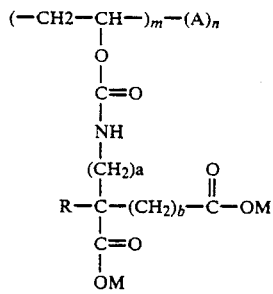

wherein a, b, R, and M are as defined above in Formula 1 and wherein A is a repeating unit comprised of at least one copolymerizable comonomer and wherein m and n represent the number of repeating units of the vinyl carbamate monomer and comonomer respectively. These comonomers include ethylenically unsaturated carboxylic acids and their salts, esters, and derivatives such as acrylic acid, methacrylate, methyl methacrylate, crotonic acid, N-methylacrylyl-D-glucosamine, vinyl benzoic acid, vinylacetic acid, itaconic acid, acrylamide, and methyl acrylamide; ethylenically unsaturated dicarboxylic acids and their salts, esters, anhydrides and derivatives such as fumaric acid, maleic acid and maleic anhydride; ethylenically unsaturated alcohols such as allyl alcohol; ethylenically unsaturated amines such as allyl amine; ethylenically unsaturated pyrrols such as N-vinylpyrrolidinone; vinyl ethers such as methyl vinyl ether; alkyl acrylates; alkenyl carboxyalkyl ethers; vinyl esters of carboxylic acids; alkenyl aryls such as vinyl benzene, polymerizable derivatives of 4-hydroxy-2,6-pyridine dicarboxylic acid; 2,6-pyridine dicarboxylic acid and and vinyl pyridine; alkenyl aldehydes such as acrolein; acrylonitrile; methacrylonitrile; olefins and furans.

The vinyl esters of alkanoic acids which may be employed are those having from one to about 13 carbon atoms and include, for example, vinyl formate, vinyl acetate, vinyl propionate, vinyl butyrate, vinyl isobutyrate, vinyl valerate, vinyl 2-ethyl-hexanoate, vinyl isooctanoate, vinyl nonoate, vinyl decanoate, vinyl pivalate, etc.

Those skilled in the art will recognize that the preferred selection of comonomers will be those comonomers best suited to the polymers intended use. Thus, for detergent use, comonomers with known effectiveness as 'hardness' ion sequestrants or as detergent builders are selected. Other factors, such as cost and detergent formulation compatibility will also guide comonomer selection.

Optionally, polyunsaturated polymerizable comonomers may also be present in small amounts, i.e., up to about 5% by weight. Such comonomers include those polyethylenically-unsaturated monomers such as lower alkenyl lower alkenoates, for example, vinyl crotonate, allyl acrylate, allyl methacrylate; di-lower alkenyl alkanedioates, for example, diallyl maleate, divinyl adipate, diallyl adipate; di-lower alkenyl benzenedicarboxylates, for example diallyl phthalate; lower alkanediol di-lower alkenoates, for example ethylene glycol diacrylate, ethylene glycol dimethacrylate, butanediol dimethacrylate; lower alkylene bis-acrylamides and lower alkylene bis-methacrylamides, for example, methylene bis-acrylamide; triallyl cyanurate, etc.

Batch, semi-batch or slow addition methods may be used to prepare the homopolymers or copolymers utilized herein. In accordance with either the batch or semi-batch procedures, the initiator(s), any optional comonomers and the novel carbamate monomer are polymerized in aqueous medium under pressures not exceeding 100 atmospheres in the presence of a catalyst, the aqueous system being maintained by a suitable buffering agent at a pH of 2 to 10, the catalyst being added incrementally or continuously. Suitable as polymerization catalysts are the water soluble free-radical formers generally used in polymerization, such as azobisisobutyronitrile (AIBN), hydrogen peroxide, sodium persulfate, potassium persulfate and ammonium persulfate, as well as tert-butyl hydroperoxide, in amounts of about 0.01 to 15% by weight, preferably about 0.01 to 1% by weight based on the total amount of monomer(s). The free-radical formers can be charged in the aqueous solution or added during the polymerization in doses.

The polymerization is carried out at a pH of between 2 and 10, preferably between 3 and 5. In order to maintain the pH range, customary buffer systems may be used. For example, alkali metal acetates, alkali metal carbonates, alkali metal phosphates and the like. Polymerization regulators, such as mercaptans, aldehydes, chloroform, methylene chloride, and trichloroethylene can also be added in some cases.

The polymers according to the invention contain at least about 5% of the repeating unit with Formula 2. Since homopolymers may be used, the actual repeating-unit content may be about 5-100%. The polymers may be copolymers, terpolymers or other higher combinations of polymerizable comonomers. In this case, the polymer contains not only repeating units of Formula 2, but also other repeating units, derived from ethylenically unsaturated comonomers in order to vary the properties of the polymer and particularly its solubility.

The polymers according to the present invention generally have a molecular weight of about 1,000 to 750,000 and preferably of about 5,000 to 400,000.

The molecular weight of the polymers can be controlled by the usual methods, for example, by varying the concentration of monomer(s), initiator(s) and chain-transfer agent(s).

It will be found that the biodegradability of selected polymers is enhanced by the incorporation into these polymers of the novel carbamate monomers of Formula I. The polymers which are expected to benefit from such introduction are generally polymers formed from ethylenically unsaturated monomers copolymerizable with vinyl acetate and/or ethylene. Examples of such monomers include ethylenically unsaturated carboxylic acids and their salts, esters, and derivatives such as acrylic acid, methacrylate, methyl methacrylate, crotonic acid, N-methylacrylyl-D-glucosamine, vinyl benzoic acid, vinylacetic acid, itaconic acid, acrylamide, and methyl acrylamide; ethylenically unsaturated dicarboxylic acids and their salts, esters, anhydrides and derivatives such as fumaric acid, maleic acid and maleic anhydride; ethylenically unsaturated alcohols such as allyl alcohol; ethylenically unsaturated amines such as allyl amine; ethylenically unsaturated pyrrols such as N-vinylpyrrolidinone; vinyl ethers such as methyl vinyl ether; alkyl acrylates alkenyl carboxyalkyl ethers; vinyl esters of carboxylic acids; alkenyl aryls such as vinyl benzene and vinyl pyridine; alkenyl aldehydes such as acrolein; acrylonitrile; methacrylonitrile; olefins and furans.

When converted into suitable form, the substantially water-soluble polymeric salts of this invention can be used as sequestering agents in a wide variety of detergent or laundry additive compositions.

Detergent compositions are generally a blend of a surfactant(s), builder(s) and, optionally, ion exchanger(s), filler(s), alkali(es), anticorrosion material(s), antiredeposition material(s), bleach(es), enzyme(s), optical brightener(s), fragrance(s) and other components selected for particular applications.

Detergent compositions incorporating the polymeric salt of the invention prepared using the processes of this invention contain as essential components from about 0.5% to about 98% of a surfactant and from about 2% to about 99.5% of the polymeric compounds as a detergency builder, generally in the sodium or ammonium salt form. Preferably the detergent composition contains, in percent by weight of the composition: (a) about 10%–60% builder including the polymeric compounds of the invention; (b) about 2%–25% surfactant, (c) optionally, 30% of other ingredients and a sufficient amount of water to either insure fluidity in the case of a liquid or to enhance processibility in the case of a solid granular or powdered detergent. Surfactants that are useful in the present invention are the anionic (soap and nonsoap), nonionic, zwitterionic and ampholytic compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and "Surface Active Agents and Detergents" by Schwartz, Perry and Berch, the disclosures of which are incorporated by reference herein.

The polymeric builder can be used either as the sole builder or, where desired, can be used in conjunction with other well-known builders, examples of which include water-soluble salts of phosphates, pyrophosphates, orthophosphates, polyphosphates, phosphonates, carbonates, carboxylates, polycarboxylates, succinates and the like.

In addition to the surfactant and builder, there may be optionally present additional ingredients which enhance the performance of the detergent composition. Typical examples of these include the well known soil suspending agents, hydrotropes, corrosion inhibitors, dyes, perfumes, fillers, optical brighteners, enzymes, suds boosters, suds depressants, germicides, anti-tarnishing agents, cationic detergents, softeners, bleaches, buffers and the like. Other ingredients which may be optionally employed are such components as coloring dyes, suds stabilizers (e.g. dibutyl phthlate), fluorescent dyes, enzymes, perfumes, antiredeposition agents (e.g. carboxymethylcellulose), soil shield agents (e.g. hydropropyl methyl cellulose), bleaches, neutralized copolymers of ethylene and maleic anhydrides (e.g. EMA resins manufactured by the Monsanto Company), co-surfactants and the like. Co-surfactants may be selected from the group consisting of anionic, cationic and zwitterionic surfactants and mixtures thereof. The bleaches may be chlorine or oxygen release types. The amounts of these additional ingredients or adjuvants may range from about 0 to 30% by weight of the composition. Some of the adjuvants may be incorporated during the slurry preparation and others, because of stability considerations, may be post added to a spray-dried product as well known to those skilled in the art.

The detergent compositions of the present invention may be in any of the usual physical forms for such compositions, such as powders, beads, flakes, bars, tablets, noodles, liquids, pastes and the like. The detergent compositions are prepared and utilized in the conventional manner. The wash solutions thereof desirably have a pH of about 7 to about 12, preferably about 9 to about 11 and contain typically about 0.05 to about 0.5% and preferably 0.09% to about 0.3% by weight of the detergent composition and a corresponding amount of the polymeric compounds of this invention, preferably, for example, about 0.005% to about 0.3% by weight.

In addition to their utility as builders in detergent and laundry additive compositions, the polymeric salts of the invention can also be utilized in other contexts wherein water hardness sequestration is required. Other uses are provided in water softening compositions, devices and methods, bleach stabilization compositions, and boiler descaling compositions and methods.

DETAILED DESCRIPTION OF THE INVENTION

Vinyl carbamates are prepared via the reaction of vinyl chloroformate and the corresponding amino acid which may be, for example, aspartic acid, N-methyl aspartic acid, aminoadipic acid, glutamic acid, 2-methyl glutamic acid or aminomalonic acid to yield the corresponding N-VOC (N-vinyloxy carbonyl) amino acid defined in Formula I. The HCl produced during the reaction is neutralized by using at least one additional equivalent of amino acid or other base. Acetonitrile, dioxane/water, or other solvent systems are used in the preparation of these novel vinyl carbamates. Reaction temperatures and times will, of course, vary for different amino acids.

Polymerization of these novel vinyl carbamates is preferably accomplished in aqueous solution at temperatures of about 5°–85° C. but preferably at temperatures of about 25°–65° C. with concentrations varying from about 1–80%. Polymerizations may be initiated with potassium persulfate but other initiators such as peroxides may also be used. The novel polymers have a molecular weight of about 1,000–>750,000. The inventive polymers were tested for their calcium binding capability.

All parts, percentages, and proportions herein and in the appended claims are by weight unless otherwise specified.

EXAMPLE 1

Monomer Synthesis

Preparation of N-Vinyloxy Carbonyl (N-VOC) Aspartic Acid

Aspartic acid (20.0 g, 0.150 mol) was added to a flask containing 180 ml of acetonitrile. Vinyl chloroformate (8.0 g, 0.075 mol) was added to the mixture and the mixture was agitated. The mixture was refluxed with continued agitation for 2 hours and cooled to room temperature. The reaction mixture was then filtered. Solvent was removed from the filtrate in vacuo to yield N-VOC aspartic acid. The product was characterized by NMR ($^1$H and $^{13}$C) and mass spectrometry. $^1$H NMR (200 MHz, acetone-$d_6$) $\delta 2.96$ (2H, dd, $-CH_2CO_2H$), 4.44, 4.71, 7.20 (3H, m, $CH_2=CH-$), 4.66 (1H, m, $-CH(CO_2H)$).

Preparation of N-VOC Glutamic Acid

Glutamic acid (20.0 g, 0.121 mol) was added to a flask containing 180 ml of acetonitrile. Vinyl chloroformate (6.4 g, 0.060 mol) was added to the mixture and the mixture was agitated. The mixture was refluxed for 2 hours with continued agitation and cooled to room temperature. The reaction mixture was then filtered. Solvent was removed from the filtrate in vacuo to yield N-VOC glutamic acid. The product was characterized by NMR ($^1$H and $^{13}$C) and mass spectrometry. $^1$H NMR (200 MHz, acetone-$d_6$) $\delta 2.08$ (2H, m, $-CH_2-$), 2.39 (2H, t, $-CH_2CO_2H$), 4.20 (1H, m, $-CH(CO_2H)-$), 4.29, 4.57, 7.04 (3H, m, $CH_2=CH-$).

EXAMPLE 2

Polymer Synthesis

A General Method for Preparing Poly(vinyl carbamates)

An aqueous solution of monomers (30–50% w/w) is sparged with a steady stream of nitrogen for 1 hour. Polymerization is initiated with potassium persulfate (1% of the total weight of monomers). The solution is stirred at ambient temperatures and then heated to a range of about 35°–70° C. until an increase in viscosity is noted. The polymer is isolated by precipitating from a non-solvent.

Preparation of Acrylic Acid/N-VOC Aspartic Acid Copolymer

Acrylic Acid (2.9 g, 0.040 mol) and N-VOC aspartic acid (2.0 g, 0.010 mol, Example 1) were dissolved in 25 ml of water. The solution was then sparged with a steady stream of nitrogen for 1 hour. Potassium persulfate (0.05 g, $1.8\times10^{-4}$ mol) was then dissolved in the solution. The solution was stirred at 70° C. for 16 hours to allow polymerization. The polymer was then isolated by precipitation in acetonitrile. The precipitated polymer in turn was analyzed by GPC and NMR ($^1$H and $^{13}$C). Nitrogen analysis of the polymer showed 11 molar % incorporation of the carbamate monomer. GPC analysis showed a molecular weight (Mw) of >750,000. Calcium binding studies of this polymer showed an upper log $K_{ca}$ value of 5.3 with unoccupied binding sites and a log $K_{ca}$ value of 4.5 with 50% of the binding sites occupied.

Preparation of Maleic Acid/N-VOC Aspartic Acid Copolymer

Maleic Acid (3.0 g, 0.026 mol) and N-VOC aspartic acid (5.2 g, 0.026 mol, Example 1) were dissolved in 25 ml of water. The solution was then sparged with a steady stream of nitrogen for 1 hour. Potassium persulfate (0.08 g, $3.0\times10^{-4}$ mol) was then dissolved in the solution. The solution was stirred at 70° C. for 16 hours to allow polymerization. The polymer was then isolated by precipitation in acetone. The precipitated polymer in turn was analyzed by GPC and NMR ($^1$H and $^{13}$C). Nitrogen analysis of the polymer showed a 50 molar % incorporation of the carbamate monomer. GPC analysis showed a molecular weight (Mw) of 100,000. Calcium binding studies of this polymer showed an upper log $K_{Ca}$ value of 6.5 with unoccupied binding sites and a log $K_{ca}$ value of 4.8 with 50% of the binding sites occupied.

Determination of Calcium Binding

Calcium binding data was obtained at a pH of 10 by titrating 100 ml of 0.05 g/l polymer solution at an ionic strength of 0.02–0.03 M (NaCl) with a 0.02 M $CaCl_2$ solution. A Radiometer calcium ion selective electrode was used to measure free $Ca^{++}$ ion concentration of the solutions. Data was corrected for dilution during each titration.

FIG. 1 reports calcium binding data for the polymers of Example 2 and other previously reported polymeric builders. Builder U (poly glyoxylic acid) was obtained from Monsanto and had a molecular weight (Mw) of 8,000. Poly acrylic acid had a molecular weight (Mw) of 60,000 and Sokolan CP7 (a 2:1 copolymer of acrylic acid/maleic acid obtained from BASF) had a molecular weight of 52,000. The actual values are reported in Table 1. The Figure shows log $K_{Ca}$ values versus the fraction of bound sites along the polymer. As polymeric sequestrants chelate hardness ions, the binding of the polymer decreases. This decrease in binding capability is illustrated in the Figure which clearly shows the binding of the novel polymeric carbamate builders to be excellent.

TABLE 1

| | A | | B | | C | | D | | E | |
|---|---|---|---|---|---|---|---|---|---|---|
| | Fraction Bound | Log $K_{ca}$ | Fraction Bound | Log $K_{ca}$ | Fraction Bound | Log $K_{ca}$ | Fraction Bound | Log $K_{ca}$ | Fraction Bound | Log $K_{ca}$ |
| 1 | 0 | 5.30 | 0 | 6.90 | 0 | 6.10 | 0 | 4.80 | 0 | 6.80 |
| 2 | 0.18 | 5.30 | 0.36 | 5.74 | 0.29 | 5.13 | 0.14 | 4.32 | 0.35 | 5.43 |
| 3 | 0.25 | 4.97 | 0.41 | 5.21 | 0.33 | 4.91 | 0.23 | 4.11 | 0.43 | 5.10 |
| 4 | 0.33 | 4.84 | 0.46 | 5.02 | 0.36 | 4.75 | 0.27 | 3.95 | 0.52 | 4.85 |
| 5 | 0.40 | 4.72 | 0.50 | 4.77 | 0.40 | 4.56 | 0.32 | 3.82 | 0.60 | 4.58 |
| 6 | 0.47 | 4.59 | 0.55 | 4.62 | 0.43 | 4.45 | 0.36 | 3.69 | 0.66 | 4.34 |
| 7 | 0.54 | 4.48 | 0.59 | 4.48 | 0.46 | 4.33 | 0.39 | 3.56 | 0.71 | 4.16 |
| 8 | 0.61 | 4.39 | 0.63 | 4.33 | 0.49 | 4.23 | 0.41 | 3.45 | 0.74 | 3.98 |
| 9 | 0.67 | 4.29 | 0.67 | 4.23 | 0.52 | 4.16 | 0.44 | 3.32 | 0.75 | 3.80 |
| 10 | 0.73 | 4.24 | 0.71 | 4.16 | 0.54 | 4.08 | 0.46 | 3.24 | 0.76 | 3.68 |

TABLE 1-continued

| | A | | B | | C | | D | | E | |
|---|---|---|---|---|---|---|---|---|---|---|
| | Fraction Bound | Log $K_{ca}$ | Fraction Bound | Log $K_{ca}$ | Fraction Bound | Log $K_{ca}$ | Fraction Bound | Log $K_{ca}$ | Fraction Bound | Log $K_{ca}$ |
| 11 | 0.82 | 4.21 | 0.78 | 4.14 | 0.59 | 3.91 | 0.47 | 3.10 | | |

A N-VOC aspartic acid/acrylic acid copolymer
B N-VOC aspartic acid/maleic acid copolymer
C Builder U
D Polyacrylate
E Sokolan CP7
*values obtained by extrapolation This invention has been described with respect to certain preferred embodiments, and various modifications and variations in the light thereof will be suggested to persons skilled in the art and are to be included within the spirit and purview of this application and the scope of the appended claims.

What is claimed is:

1. Polymeric compounds of the Formula:

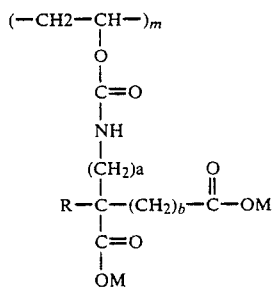

wherein a and b are independently 0, 1, or 2 or even greater; m is at least one; R is hydrogen, methyl, ethyl, or long chain alkyl, alkenyl or aryl and M is $C_{1-4}$ alkyl, hydrogen, or a cation which forms a substantially water soluble salt with said polymeric compound at ambient temperatures.

2. Compounds as defined in claim 1 wherein a and b are independently 0, 1, or 2; wherein R is hydrogen or methyl and wherein M is hydrogen, ammonium or alkali metal.

3. Compounds as defined in claim 1 wherein a is 0, b is 0 or 2 and R is hydrogen.

4. Compounds as defined in claim 1 wherein a is 0, b is 1, and R is hydrogen or methyl.

5. A compound as defined in claim 1 wherein a is 1, b is 0, and R is hydrogen.

6. A polymer as defined in claim 1 having substantial water solubility and a molecular weight of about 1000 to about 750,000.

7. Compounds as defined in claim 1 having a log $K_{Ca}$ of greater than about 4.

8. Polymeric compounds comprising repeating units of the structure:

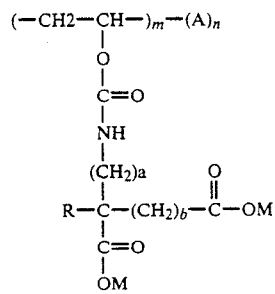

wherein a and b are independently 0, 1, or 2 or even greater; wherein m and n are at least one; wherein m is at least 5% of the total of m+n R is hydrogen, methyl, ethyl, or long chain alkyl, alkenyl or aryl and M is hydrogen or a cation which forms a substantially water soluble salt with said polymeric compound at ambient temperatures or $C_{1-4}$ alkyl and wherein A is a repeating unit comprised of at least one copolymerized comonomer, said comonomers being selected from the group consisting of unsaturated carboxylic acids and their salts, esters and derivatives, unsaturated dicarboxylic acids and their salts, esters, and derivatives, unsaturated alcohols, unsaturated amines, unsaturated pyrrols, vinyl ethers, alkyl acrylates, alkenyl carboxyalkyl ethers, vinyl esters of carboxylic acids, olefins and furans.

9. The polymer of claim 8 wherein the comonomer is acrylic acid.

10. The polymer of claim 8 wherein the comonomer is methacrylic acid.

11. The polymer of claim 8 wherein the comonomer is crotonic N-methylacrylyl-D-glucosamine.

12. The polymer of claim 8 wherein the comonomer is N-methylacrylyl-D-glucosamine.

13. The polymer of claim 8 wherein the comonomer is vinyl benzoic acid.

14. The polymer of claim 8 wherein the comonomer is methyl acrylate.

15. The polymer of claim 8 wherein the comonomer is itaconic acid.

16. The polymer of claim 8 wherein the comonomer is acrylamide.

17. The polymer of claim 8 wherein the comonomer is mesaconic acid.

18. The polymer of claim 8 wherein the comonomer is methyl acrylamide.

19. The polymer of claim 8 wherein the comonomer is fumaric acid.

20. The polymer of claim 8 wherein the comonomer is maleic acid.

21. The polymer of claim 8 wherein the comonomer is maleic anhydride.

22. The polymer of claim 8 wherein the comonomer is allyl alcohol.

23. The polymer of claim 8 wherein the comonomer is allyl amine.

24. The polymer of claim 8 wherein the comonomer is N-vinylpyrrolidinone.

25. The polymer of claim 8 wherein the comonomer is vinyl acetate.

26. The polymer of claim 8 wherein the comonomer is methyl methacrylate.

27. The polymer of claim 8 wherein the comonomer is methyl vinyl ether.

28. The polymer of claim 8 wherein the comonomer is vinyl benzene.

29. The polymer of claim 8 wherein the comonomer is vinyl pyridine.

30. The polymer of claim 8 wherein the comonomer is a polymerizable derivate of 4 hydroxy 2,6 pyridine dicarboxylic acid.

31. The polymer of claim 8 wherein the comonomer is a polymerizable derivative of 2,6 pyridine dicarboxylic acid.

32. The polymer of claim 8 wherein the comonomer is acrolein.

33. The polymer of claim 8 wherein the comonomer is acrylonitrile.

34. The polymer of claim 8 wherein the comonomer is methacrylonitrile.

35. Compounds as defined in claim 8 having a log $K_{Ca}$ of greater than about 4.

36. A detergent composition comprising about 0.5% to about 98% of a surfactant and about 2% to about 99.5% of the polymeric builder of claim 1.

37. A detergent composition comprising about 0.5% to about 98% of a surfactant and about 2% to about 99.5% of the polymeric builder of claim 8.

38. A wash solution containing about 0.5% to about 0.05% by weight of the detergent composition of claim 36.

39. A wash solution containing about 0.5% to about 0.05% by weight of the detergent composition of claim 37.

40. Polymeric compounds of the Formula:

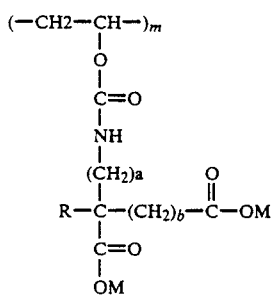

wherein a and b are independently 0, 1, or 2 or even greater; m is at least one; R is hydrogen, methyl, ethyl, or long chain alkenyl or aryl and M is $C_{1-4}$ alkyl, hydrogen, or a cation which forms a substantially water soluble salt with said polymeric compound at ambient temperatures whereby the carbamate linkage enhances the biodegradability of said polymer.

41. Polymeric compounds comprising repeating units of the structure:

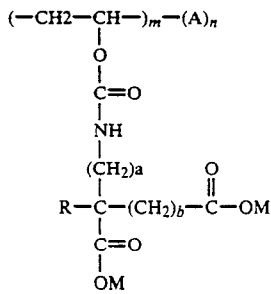

wherein a and b are independently 0, 1, or 2 or even greater; wherein m and n are at least one; R is hydrogen, methyl, ethyl, or long chain alkyl, alkenyl or aryl and M is $C_{1-4}$ alkyl, hydrogen, or a cation which forms a substantially water soluble salt with said polymeric compound at ambient temperatures and wherein A is a repeating unit comprised of at least one copolymerized comonomer, said comonomers being selected from the group consisting of unsaturated carboxylic acids, unsaturated dicarboxylic acids, unsaturated alcohols, unsaturated amines, unsaturated pyrrols, vinyl ethers, alkyl acrylates, alkenyl carboxyalkyl ethers, vinyl esters of carboxylic acids, olefins and furans whereby the carbamate linkage enhances the biodegradability of said polymer.

42. A method for enhancing the biodegradability of polymers formed from ethylenically unsaturated monomers by introducing into said polymers the monomers defined in claim 1.

43. A method as defined in claim 40 wherein said polymers are selected from the group consisting of ethylenically unsaturated monomers copolymerizable with vinyl acetate and/or ethylene.

44. A method as defined in claim 41 wherein said ethylenically unsaturated monomers are selected from the group consisting of ethylenically unsaturated carboxylic acids, ethylenically unsaturated carboxylic acid salts; ethylenically unsaturated carboxylic acid esters, ethylenically unsaturated dicarboxylic acids, salts, esters, and anhydrides of ethylenically unsaturated dicarboxylic acids, ethylenically unsaturated alcohols, ethylenically unsaturated amines, ethylenically unsaturated pyrrols, vinyl ether, alkyl acrylates, alkenyl carboxyalkyl ethers, vinyl esters of carboxylic acids, alkenyl aryls, alkenyl aldehydes, acrylonitrile, metharylonitrile, olefins and furans.

45. A method as defined in claim 42 wherein said ethylenically unsaturated monomers are selected from the group consisting of acrylic acid, methacrylic acid, methyl methacrylate, methyl acrylate, crotonic acid, N-methylacrylyl-D-glucosamine, vinyl benzoic acid, vinylacetic acid, itaconic acid, acrylamide, methyl acrylamide, fumaric acid, maleic acid, maleic anhydride, allyl alcohol, allyl amine, N-vinylpyrrolidinone, methyl vinyl ether, vinyl benzene, vinyl pyridine, and acrolein.

46. The compound of claim 1 for use as a detergency builder.

47. The compound of claim 8 for use as a detergency builder.

48. A method for building a detergent composition comprising adding about 2 to about 99.5% of the compound of claim 7 to said detergent composition.

49. A method for building a detergent composition comprising adding about 2 to about 99.5% of the compound of claim 14 to said detergent composition.

* * * * *